United States Patent

Blasco et al.

(10) Patent No.: US 6,855,718 B2
(45) Date of Patent: Feb. 15, 2005

(54) 7-(R)-AMINOTRIAZOLOPYRIMIDINES, THE PRODUCTION THEREOF AND USE OF THE SAME FOR COMBATTING PHYTOPATHOGENIC FUNGI

(75) Inventors: Jordi Tormo i Blasco, Limburgerhof (DE); Klaus Ditrich, Gönnheim (DE); Hubert Sauter, Mannheim (DE); Oliver Cullmann, Heppenheim (DE); Markus Gewehr, Kastellaun (DE); Wassilios Grammenos, Ludwigshafen (DE); Bernd Müller, Frankenthal (DE); Thomas Grote, Wachenheim (DE); Andreas Gypser, Mannheim (DE); Joachim Rheinheimer, Ludwigshafen (DE); Ingo Rose, Mannheim (DE); Peter Schäfer, Ottersheim (DE); Frank Schieweck, Hessheim (DE); Eberhard Ammermann, Heppenheim (DE); Siegfried Strathmann, Limburgerhof (DE); Gisela Lorenz, Hambach (DE); Reinhard Stierl, Mutterstadt (DE)

(73) Assignee: BASF Aktiengesellschaft, Ludwigshafen (DE)

( * ) Notice: Subject to any disclaimer, the term of this patent is extended or adjusted under 35 U.S.C. 154(b) by 0 days.

(21) Appl. No.: 10/416,467
(22) PCT Filed: Nov. 9, 2001
(86) PCT No.: PCT/EP01/12977
§ 371 (c)(1), (2), (4) Date: May 12, 2003
(87) PCT Pub. No.: WO02/38565
PCT Pub. Date: May 16, 2002

(65) Prior Publication Data
US 2004/0110771 A1 Jun. 10, 2004

(30) Foreign Application Priority Data
Nov. 13, 2000 (DE) .......................... 100 56 101

(51) Int. Cl.⁷ ..................... C07D 487/04; A01N 43/90
(52) U.S. Cl. ................................ 514/259.31; 544/263
(58) Field of Search ...................... 514/259.31; 544/263

(56) References Cited

U.S. PATENT DOCUMENTS

| 5,981,534 A | * 11/1999 | Pfrengle ............... 514/259.31 |
| 5,985,883 A | 11/1999 | Pees ........................ 514/258 |
| 5,986,135 A | * 11/1999 | Pfrengle et al. ............ 564/303 |
| 6,117,876 A | 9/2000 | Pees et al. ................ 514/258 |

FOREIGN PATENT DOCUMENTS

| EP | 945 453 | 9/1999 |
| FR | 2 784 381 | 4/2000 |
| WO | 98/46607 | 10/1998 |
| WO | WO 2003008417 A1 * | 1/2003 |

* cited by examiner

Primary Examiner—Thomas C. McKenzie
(74) Attorney, Agent, or Firm—Keil & Weinkauf

(57) ABSTRACT

A 7-(R)-Aminotriazolopyrimidines of formula I

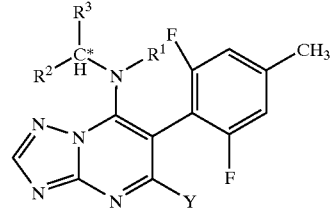

where the substituents and index are as defined below:

$R^1$ is hydrogen or methyl;

$R^2$ is methyl;

$R^3$ is $C_2$–$C_{10}$-alkyl, $C_1$–$C_4$-alkoxymethyl, $C_3$–$C_{10}$-cycloalkyl;

Y is halogen, cyano, $C_1$–$C_4$-alkyl or $C_1$–$C_4$-alkoxy;

where * is a center of chirality in the R configuration, processes for their preparation, compositions comprising them and their use for controlling harmful fungi.

8 Claims, No Drawings

7-(R)-AMINOTRIAZOLOPYRIMIDINES, THE PRODUCTION THEREOF AND USE OF THE SAME FOR COMBATTING PHYTOPATHOGENIC FUNGI

The invention relates to 7-(R)-aminotriazolopyrimidines of the formula I

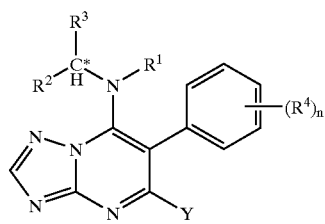

where the substituents and the index are as defined below:
$R^1$ is hydrogen or methyl;
$R^2$ is methyl;
$R^3$ is $C_2$–$C_{10}$-alkyl, $C_1$–$C_4$-alkoxymethyl, $C_3$–$C_{10}$-cycloalkyl;
$R^4$ is halogen, $C_1$–$C_4$-alkyl, $C_1$–$C_4$-haloalkyl or $C_1$–$C_4$-alkoxy;
n is a number from 1 to 5;
Y is halogen, cyano, $C_1$–$C_4$-alkyl or $C_1$–$C_4$-alkoxy;
where * is a center of chirality in the R configuration.

Furthermore, the invention relates to a process for preparing the compounds of the formula I, to compositions for controlling phytopathogenic fungi, which compositions comprise the compounds I, and to the use of the compounds I for controlling phytopathogenic fungi.

WO-A 98/46607 Discloses Racemic
5-chloro-7-amino-6-(2,4,6-trifluorophenyl)-1,2,4-triazolo[1,5-a]-pyrimidines. Furthermore, on page 7, paragraphs 1 and 2, of WO-A 98/46607, it is mentioned quite generally that, in the case of compounds having a chiral amine moiety, the respective S-enantiomers would in each case have particularly interesting fungicidal properties.

WO-A 98/46608 Discloses Racemic
5-halo-7-(fluoroalkyl)amino-6-phenyl-1,2,4-triazolo[1,5-a]pyrimidines, where the α-C-atom of the 7-(fluoroalkyl)amino moiety is chiral and carries a $CF_3$ group. In this publication, it is taught that the respective S-enantiomers would in each case have particularly interesting fungicidal properties.

It is an object of the present invention to provide compounds having improved activity and/or a broader activity spectrum.

Surprisingly, we have found that this object is achieved by compounds carrying a R-configured halogen-free amino radical in the 7-position.

The meanings listed above are collective terms for individual enumerations of the individual group members. All carbon chains can be straight-chain or branched. Halogenated substituents preferably carry 1 to 5 identical or different halogen atoms.

In the definitions of the symbols given in the formulae above, collective terms are used which, in general, represent the following substituents:
halogen: fluorine, chlorine, bromine and iodine;
alkyl: saturated straight-chain or branched hydrocarbon radicals having 1 to 4, 6, 8 or 10 carbon atoms, for example $C_1$–$C_6$-alkyl, such as methyl, ethyl, propyl, 1-methylethyl, butyl, 1-methylpropyl, 2-methylpropyl, 1,1-dimethylethyl, pentyl, 1-methylbutyl, 2-methylbutyl, 3-methylbutyl, 2,2-dimethylpropyl, 1-ethylpropyl, hexyl, 1,1-dimethylpropyl, 1,2-dimethylpropyl, 1-methylpentyl, 2-methylpentyl, 3-methylpentyl, 4-methylpentyl, 1,1-dimethylbutyl, 1,2-dimethylbutyl, 1,3-dimethylbutyl, 2,2-dimethylbutyl, 2,3-dimethylbutyl, 3,3-dimethylbutyl, 1-ethylbutyl, 2-ethylbutyl, 1,1,2-trimethylpropyl, 1,2,2-trimethylpropyl, 1-ethyl-1-methylpropyl and 1-ethyl-2-methylpropyl;

alkoxy: straight-chain or branched alkyl groups having 1 to 4 carbon atoms (as mentioned above) which are attached to the skeleton via an oxygen atom (—O—);

alkenyl: unsaturated straight-chain or branched hydrocarbon radicals having 2 to 4, 6, 8 or 10 carbon atoms and a double bond in any position, for example $C_2$–$C_6$-alkenyl, such as ethenyl, 1-propenyl, 2-propenyl, 1-methylethenyl, 1-butenyl, 2-butenyl, 3-butenyl, 1-methyl-1-propenyl, 2-methyl-1-propenyl, 1-methyl-2-propenyl, 2-methyl-2-propenyl, 1-pentenyl, 2-pentenyl, 3-pentenyl, 4-pentenyl, 1-methyl-1-butenyl, 2-methyl-1-butenyl, 3-methyl-1-butenyl, 1-methyl-2-butenyl, 2-methyl-2-butenyl, 3-methyl-2-butenyl, 1-methyl-3-butenyl, 2-methyl-3-butenyl, 3-methyl-3-butenyl, 1,1-dimethyl-2-propenyl, 1,2-dimethyl-1-propenyl, 1,2-dimethyl-2-propenyl, 1-ethyl-1-propenyl, 1-ethyl-2-propenyl, 1-hexenyl, 2-hexenyl, 3-hexenyl, 4-hexenyl, 5-hexenyl, 1-methyl-1-pentenyl, 2-methyl-1-pentenyl, 3-methyl-1-pentenyl, 4-methyl-1-pentenyl, 1-methyl-2-pentenyl, 2-methyl-2-pentenyl, 3-methyl-2-pentenyl, 4-methyl-2-pentenyl, 1-methyl-3-pentenyl, 2-methyl-3-pentenyl, 3-methyl-3-pentenyl, 4-methyl-3-pentenyl, 1-methyl-4-pentenyl, 2-methyl-4-pentenyl, 3-methyl-4-pentenyl, 4-methyl-4-pentenyl, 1,1-dimethyl-2-butenyl, 1,1-dimethyl-3-butenyl, 1,2-dimethyl-1-butenyl, 1,2-dimethyl-2-butenyl, 1,2-dimethyl-3-butenyl, 1,3-dimethyl-1-butenyl, 1,3-dimethyl-2-butenyl, 1,3-dimethyl-3-butenyl, 2,2-dimethyl-3-butenyl, 2,3-dimethyl-1-butenyl, 2,3-dimethyl-2-butenyl, 2,3-dimethyl-3-butenyl, 3,3-dimethyl-1-butenyl, 3,3-dimethyl-2-butenyl, 1-ethyl-1-butenyl, 1-ethyl-2-butenyl, 1-ethyl-3-butenyl, 2-ethyl-1-butenyl, 2-ethyl-2-butenyl, 2-ethyl-3-butenyl, 1,1,2-trimethyl-2-propenyl, 1-ethyl-1-methyl-2-propenyl, 1-ethyl-2-methyl-1-propenyl and 1-ethyl-2-methyl-2-propenyl;

alkynyl: straight-chain or branched hydrocarbon groups having 2 to 4, 6, 8 or 10 carbon atoms and a triple bond in any position, for example $C_2$–$C_6$-alkynyl, such as ethynyl, 1-propynyl, 2-propynyl, 1-butynyl, 2-butynyl, 3-butynyl, 1-methyl-2-propynyl, 1-pentynyl, 2-pentynyl, 3-pentynyl, 4-pentynyl, 1-methyl-2-butynyl, 1-methyl-3-butynyl, 2-methyl-3-butynyl, 3-methyl-1-butynyl, 1,1-dimethyl-2-propynyl, 1-ethyl-2-propynyl, 1-hexynyl, 2-hexynyl, 3-hexynyl, 4-hexynyl, 5-hexynyl, 1-methyl-2-pentynyl, 1-methyl-3-pentynyl, 1-methyl-4-pentynyl, 2-methyl-3-pentynyl, 2-methyl-4-pentynyl, 3-methyl-1-pentynyl, 3-methyl-4-pentynyl, 4-methyl-1-pentynyl, 4-methyl-2-pentynyl, 1,1-dimethyl-2-butynyl, 1,1-dimethyl-3-butynyl, 1,2-dimethyl-3-butynyl, 2,2-dimethyl-3-butynyl, 3,3-dimethyl-1-butynyl, 1-ethyl-2-butynyl, 1-ethyl-3-butynyl, 2-ethyl-3-butynyl and 1-ethyl-1-methyl-2-propynyl;

cycloalkyl: monocyclic saturated hydrocarbon groups having 3 to 10 carbon ring members, for example $C_3$–$C_8$-cycloalkyl, such as cyclopropyl, cyclobutyl, cyclopentyl, cyclohexyl, cycloheptyl and cyclooctyl.

The compounds I can preferably be prepared by reacting a 7-halotriazolopyrimidine of the formula II in which the substituents $R^4$ and Y and the index n are as defined in claim 1 with (R)-configured amines of the formula III.

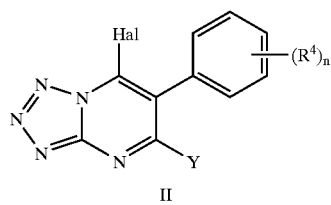 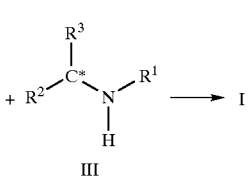

The reaction of the compound II with (R)-configured amines of the formula III is carried out, for example, in an inert solvent or diluent, such as a chlorinated hydrocarbon (in particular dichloromethane or trichloromethane), acetone, acetonitrile, dimethyl sulfoxide, dimethylformamide, N-methylpyrrolidone, an aromatic hydrocarbon (in particular toluene or chlorobenzene) or an ether (in particular tetrahydrofuran, dimethoxyethane or dioxane).

In general, the reaction is carried out using a base (for example sodium carbonate, potassium carbonate, sodium hydroxide, potassium hydroxide, sodium hydride, potassium hydride or, in particular, a tertiary amine). Tertiary amines such as triethylamine, ethyldiisopropylamine or diazabicycloundecene have been found to be particularly suitable. The bases are generally employed in equimolar amounts or in excess. Moreover, it may be advantageous to add a catalytic amount of a crown ether (for example 18-crown-6 or 15-crown-5).

The reaction temperature is generally in the range from 0 to 100° C., preferably from 10 to 35° C. The reaction can, for example, be carried out at room temperature.

To isolate and purify the compounds according to the invention, it is possible to use customary methods such as extraction, chromatography or recrystallization.

The 7-halotriazolopyrimidines II required for preparing the compounds I are known from the literature or can be prepared by methods known from the literature [cf. WO-A 98/46607; EP-A 550 113]. They are usually prepared by reacting 3-amino-1,2,4-triazole with 2-phenylmalonic esters or 2-phenylacetic esters of the formula IV

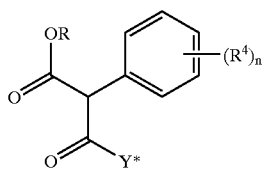

a) Y* = OR
b) Y* = R in which $R^4$ and the index n are as defined for formula I and R is $C_1$–$C_4$-alkyl. In this manner, it is possible, starting from 2-phenylmalonic esters (IVa) or diketones (IVb), to obtain 5,7-dihydroxy-6-phenyltriazolopyrimidines and 5-alkyl-7-hydroxy-6-phenyltriazolopyrimidines, respectively. If the easily accessible 2-phenylacetoacetic esters (IVb where R=CH$_3$) are used, 5-methyl-7-hydroxy-6-phenyltriazolopyrimidines are obtained [cf. Chem. Pharm. Bull. 9 (1961), 801]. The preparation of the starting materials IV is described in EP-A 10 02 788.

The resulting 5,7-dihydroxy-6-phenyltriazolopyrimidines and 5-alkyl-7-hydroxy-6-phenyltriazolopyrimidines are reacted with halogenating agents to give the 7-halotriazolopyrimidines of the formula II. Preference is given to using chlorinating or brominating agents, such as phosphorus oxybromide, phosphorus oxychloride, thionyl chloride, thionyl bromide or sulfuryl chloride. The reaction can be carried out in the absence or presence of a solvent. Customary reaction temperatures are from 0 to 150° C., preferably from 80 to 125° C.

It is furthermore possible to prepare compounds I in which Y is alkyl by the method described in U.S. Pat. No. 5,994,360—starting from 5,7-dichloro-6-phenyltriazolopyrimidines, by chlorine/amine exchange in the 7-position and substitution of the chorine by a malonic acid radical, followed by decarboxylation.

Compounds I in which Y is methoxy can be prepared advantageously by the process described in WO-A 99/41255—starting from 5,7-dichloro-6-phenyltriazolopyrimidines, by chlorine/amine exchange in the 7-position and substitution of the chlorine by methoxide.

R-configured amines III can be prepared advantageously by the route shown in scheme 1 using (R)-3,3-dimethylbut-2-amine (R-DMBA) as an example.

Scheme 1:

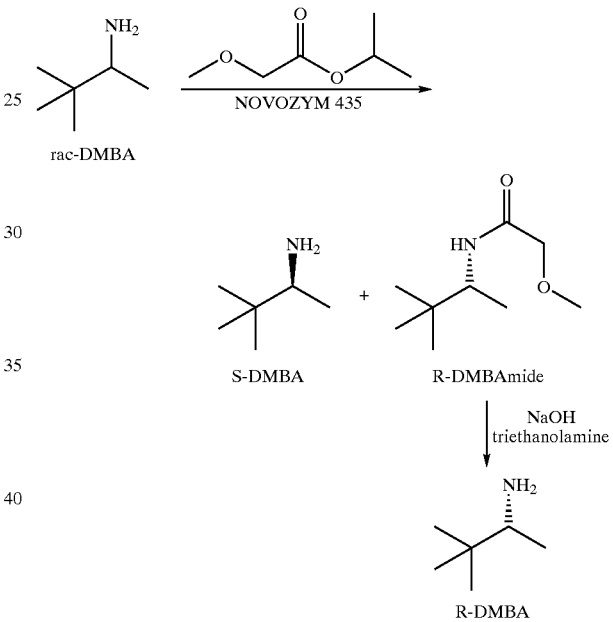

The above synthesis uses racemic 3,3-dimethylbut-2-amine (rac-DMBA), which is obtainable as described in J. Am. Chem. Soc., 1939(61), p. 3500 and J. Am. Chem. Soc., 1941(63), p. 3135, as starting material. Resolution of the racemate is carried out by the process described in WO-A 95/08636 and WO-A 97/10201. This process involves the following steps:

1) racemic 3,3-dimethylbut-2-ylamine is enantioselectively acylated in the presence of a hydrolase, using an ester whose acid component carries a fluorine, nitrogen, oxygen or sulfur atom in the vicinity of the carbonyl carbon,
2) the mixture of (S)-3,3-dimethylbut-2-ylamine (S-DMBA) and acylated (R)-3,3-dimethylbut-2-ylamine (R-DMBamide) is then separated and
3) the acylated (R)-3,3-dimethylbut-2-ylamine is subjected to amide cleavage.

The publications WO-A 95/08636 and WO-A 97/10201 give a specific list of the esters and hydrolases which are particularly suitable for racemate resolution, so that an explicit illustration can be dispensed with here.

The hydrolases used are preferably proteases and in particular lipases. Particularly suitable are lipases from *Pseudomonas*, for example Amano P, or the lipase from *Pseudomonas* spec. DSM 8246. Other particularly suitable hydrolases are the enzymes available from Novo Nordisk (Enzyme Toolbox), in particular the lipases SP 523, SP 524, SP 525, SP 526 and Novozym® 435.

The enzyme can be used in native or immobilized form.

Amines of the formula III are either commercially available or can be obtained by optical resolution of the racemate as illustrated in scheme 1.

Preference is given to compounds I in which $R^1$ is hydrogen or methyl, in particular hydrogen.

Moreover, preference is given to compounds I in which $R^2$ is methyl.

In addition, preference is also given to compounds of the formula IA:

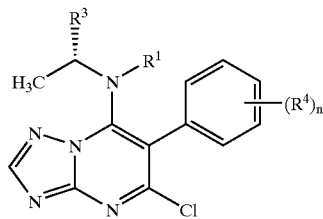

IA

In the formula IA, $R^1$, $R^3$ and $(R^4)_n$ are as defined for formula I.

Likewise, preference is given to compounds I and IA in which $R^3$ is ethyl, isopropyl or tert-butyl, in particular tert-butyl.

Preference is given to compounds of the formula I in which n is 2 or 3, in particular 3.

The substituents and the index n in the formula I are preferably as defined below:

$R^4$ is fluorine, chlorine, methyl or methoxy, in particular fluorine;

n is the number 2 or 3, in particular the number 3;

Y is fluorine, chlorine, bromine, methyl or methoxy, in particular chlorine.

With respect to $(R^4)_n$, particular preference is given to the following combinations of substituents:

2,6-difluoro;
2-chloro, 6-fluoro;
2,6-dichloro;
2-methyl-4-fluoro;
2-methyl-6-fluoro;
2,4,6-trifluoro;
2,6-difluoro-4-methyl; 2,6-difluoro-4-methoxy;
pentafluoro.

Particular preference is given to the compound (R)-5-chloro-7-(3,3-dimethylbut-2-yl)amino-6-(2,4,6-trifluorophenyl)-1,2,4-triazolo[1,5-a]pyrimidine.

In particular with a view to their use, preference is given to the compounds I compiled in the tables below. Moreover, the groups mentioned for a substituent in the tables are on their own, independently of the combination in which they are mentioned, a particularly preferred embodiment of the substituent in question.

Table 1
Compounds of the formula IA in which $R^1$ is hydrogen, $R^3$ is ethyl and the combination of the radicals $(R^4)_n$ for a compound corresponds in each case to one row of Table A Table 2
Compounds of the formula IA in which $R^1$ is hydrogen, $R^3$ is isopropyl and the combination of the radicals $(R^4)_n$ for a compound corresponds in each case to one row of Table A Table 3
Compounds of the formula IA in which $R^1$ is hydrogen, $R^3$ is tert-butyl and the combination of the radicals $(R^4)_n$ for a compound corresponds in each case to one row of Table A Table 4
Compounds of the formula IA in which $R^1$ is hydrogen, $R^3$ is n-propyl and the combination of the radicals $(R^4)_n$ for a compound corresponds in each case to one row of Table A Table 5
Compounds of the formula IA in which $R^1$ is hydrogen, $R^3$ is n-butyl and the combination of the radicals $(R^4)_n$ for a compound corresponds in each case to one row of Table A Table 6
Compounds of the formula IA in which $R^1$ is hydrogen, $R^3$ is n-pentyl and the combination of the radicals $(R^4)_n$ for a compound corresponds in each case to one row of Table A Table 7
Compounds of the formula IA in which $R^1$ is hydrogen, $R^3$ is n-hexyl and the combination of the radicals $(R^4)_n$ for a compound corresponds in each case to one row of Table A Table 8
Compounds of the formula IA in which $R^1$ is hydrogen, $R^3$ is n-heptyl and the combination of the radicals $(R^4)_n$ for a compound corresponds in each case to one row of Table A Table 9
Compounds of the formula IA in which $R^1$ is hydrogen, $R^3$ is n-octyl and the combination of the radicals $(R^4)_n$ for a compound corresponds in each case to one row of Table A Table 10
Compounds of the formula IA in which $R^1$ is hydrogen, $R^3$ is n-nonyl and the combination of the radicals $(R^4)_n$ for a compound corresponds in each case to one row of Table A Table 11
Compounds of the formula IA in which $R^1$ is hydrogen, $R^3$ is isobutyl and the combination of the radicals $(R^4)_n$ for a compound corresponds in each case to one row of Table A Table 12
Compounds of the formula IA in which $R^1$ is hydrogen, $R^3$ is cyclopropyl and the combination of the radicals $(R^4)_n$ for a compound corresponds in each case to one row of Table A Table 13
Compounds of the formula IA in which $R^1$ is hydrogen, $R^3$ is cyclohexyl and the combination of the radicals $(R^4)_n$ for a compound corresponds in each case to one row of Table A Table 14
Compounds of the formula IA in which $R^1$ is hydrogen, $R^3$ is methoxymethyl and the combination of the radicals $(R^4)_n$ for a compound corresponds in each case to one row of Table A Table 15
Compounds of the formula IA in which $R^1$ is methyl, $R^3$ is ethyl and the combination of the radicals $(R^4)_n$ for a compound corresponds in each case to one row of Table A Table 16
Compounds of the formula IA in which $R^1$ is methyl, $R^3$ is n-hexyl and the combination of the radicals $(R^4)_n$ for a compound corresponds in each case to one row of Table A

TABLE A

| No. | $(R^4)_n$ |
|---|---|
| A-1 | 2-Cl-6-F |
| A-2 | 2,6-F$_2$ |
| A-3 | 2,6-Cl$_2$ |
| A-4 | 2-CH$_3$-6-F |
| A-5 | 2,4,6-F$_3$ |
| A-6 | 2,6-F$_2$-4-OCH$_3$ |
| A-7 | F$_5$ |
| A-8 | 2-CH$_3$-4-F |
| A-9 | 2-CF$_3$ |
| A-10 | 2-OCH$_3$-6-F |
| A-11 | 2-OCH$_3$-4,6-F$_2$ |

The novel compounds I have excellent activity against a broad spectrum of phytopathogenic fungi, especially from the classes of *Ascomycetes* and *Basidiomycetes*, and they can be employed as foliar- and soil-acting fungicides. Some of them have remarkably high systemic mobility and activity after soil application and in particular also after foliar application.

They are especially important for controlling a large number of fungi in a variety of crop plants such as wheat, rye, barley, oats, rice, corn, grass, bananas, cotton, soy, coffee, sugar cane, grapevines, fruit species, ornamentals and vegetable species such as cucumbers, beans, tomatoes, potatoes and cucurbits, and also in the seeds of these plants.

Specifically, they are suitable for controlling the following plant diseases:

*Alternaria* species, *Podosphaera* species, *Sclerotinia* species, *Physalospora* canker in vegetables and fruit,
*Botrytis cinerea* (gray mold) in strawberries, vegetables, ornamentals and grapevines,
*Corynespora cassiicola* in cucumbers,
*Colletotrichum* species in fruit and vegetables,
*Diplocarpon rosae* in roses,
*Elsinoe fawcetti* and *Diaporthe citri* in citrus fruits,
*Sphaerotheca* species in cucurbits, strawberries and roses,
*Cercospora* species in groundnuts, sugar beet and aubergines,
*Erysiphe cichoracearum* in cucurbits,
*Leveillula taurica* in peppers, tomatoes and aubergines,
*Mycosphaerella* species in apples and Japanese apricot,
*Phyllactinia kakicola*, *Gloesporium kaki*, in Japanese apricot,
*Gymnosporangium yamadae*, *Leptothyrium pomi*, *Podosphaera leucotricha* and *Gloedes pomigena* in apples,
*Cladosporium carpophilum* in pears and Japanese apricot,
*Phomopsis* species in pears,
*Phytophthora* species in citrus fruits, potatoes, onions, in particular *Phytophthora infestans* in potatoes and tomatoes,
*Blumeria graminis* (powdery mildew) in cereals,
*Fusarium* and *Verticillium* species in a variety of plants,
*Glomerella cingulata* in tea,
*Drechslera* and *Bipolaris* species in cereals and rice,
*Mycosphaerella* species in bananas and groundnuts,
*Plasmopara viticola* in grapevines,
*Personospora* species in onions, spinach and chrysanthemums,
*Phaeoisariopsis vitis* and *Sphaceloma ampelina* in grapefruits,
*Pseudocercosporella herpotrichoides* in wheat and barley,
*Pseudoperonospora* species in hops and cucumbers,
*Puccinia* species and *Typhula* species in cereals and lawns,
*Pyricularia oryzae* in rice,
*Rhizoctonia* species in cotton, rice and lawns,
*Stagonospora nodorum* and *Septoria tritici* in wheat,
*Uncinula necator* in grapevines,
*Ustilago* species in cereals and sugar cane and
*Venturia* species (scab) in apples and pears.

The compounds I are also suitable for controlling harmful fungi such as *Paecilomyces variotii* in the protection of materials (for example wood, paper, paint dispersions, fibers or tissues) and in the protection of stored products.

The compounds I are employed by treating the fungi or the plants, seeds, materials or the soil to be protected against fungal attack with a fungicidally effective amount of the active compounds. The application may be carried out before or after the infection of the materials, plants or seeds by the fungi.

The fungicidal compositions generally comprise from 0.1 to 95, preferably from 0.5 to 90, % by weight of active compound.

For use in crop protection, the application rates are, depending on the kind of effect desired, from 0.01 to 2.0 kg of active compound per ha.

The treatment of seeds generally requires active compound quantities of from 0.001 to 0.1 g, preferably from 0.01 to 0.05 g, per kilogram of seed.

For use in the protection of materials or stored products, the active compound application rate depends on the kind of application area and desired effect. Customary application rates in the protection of materials are, for example, from 0.001 g to 2 kg, preferably from 0.005 g to 1 kg, of active compound per cubic meter of treated material.

The compounds I can be converted into the customary formulations, e.g. solutions, emulsions, suspensions, dusts, powders, pastes and granules. The use form depends on the specific intended use; in any case, it should ensure fine and uniform distribution of the compound according to the invention.

The formulations are prepared in a known manner, e.g. by extending the active compound with solvents and/or carriers, if desired using emulsifiers and dispersants, it also being possible to use other organic solvents as auxiliary solvents if the diluent used is water. Suitable auxiliaries for this purpose are essentially: solvents such as aromatics (e.g. xylene), chlorinated aromatics (e.g. chlorobenzenes), paraffins (e.g. mineral oil fractions), alcohols (e.g. methanol, butanol), ketones (e.g. cyclohexanone), amines (e.g. ethanolamine, dimethylformamide) and water; carriers such as ground natural minerals (e.g. kaolins, clays, talc, chalk) and ground synthetic minerals (e.g. finely divided silica, silicates); emulsifiers such as nonionic and anionic emulsifiers (e.g. polyoxyethylene fatty alcohol ethers, alkylsulfonates and arylsulfonates), and dispersants such as lignosulfite waste liquors and methylcellulose.

Suitable surfactants are the alkali metal, alkaline earth metal, and ammonium salts of lignosulfonic acid, naphthalenesulfonic acid, phenolsulfonic acid, dibutylnaphthalenesulfonic acid, alkylarylsulfonates, alkylsulfates, alkylsulfonates, fatty alcohol sulfates and fatty acids and alkali metal salts and alkaline earth metal salts thereof, salts of sulfated fatty alcohol glycol ethers, condensation products of sulfonated naphthalene and naphthalene derivatives with formaldehyde, condensation products of naphthalene or of naphthalene sulfonic acid with phenol and formaldehyde, polyoxyethylene octylphenol ethers, ethoxylated isooctylphenol, octylphenol, nonylphenol, alkylphenol polyglycol ethers, tributylphenyl polyglycol ethers, alkylaryl polyether alcohols, isotridecyl alcohol, fatty alcohol ethylene oxide condensates, ethoxylated castor oil, polyoxyethylene alkyl ethers, ethoxylated polyoxypropylene, lauryl alcohol polyglycol ether acetal, sorbitol esters, lignosulfite waste liquors and methylcellulose.

Suitable for preparing directly sprayable solutions, emulsions, pastes or oil dispersions are petroleum fractions having medium to high boiling points, such as kerosene or diesel fuel, furthermore coal-tar oils and oils of plant or animal origin, aliphatic, cyclic and aromatic hydrocarbons, for example benzene, toluene, xylene, paraffin, tetrahydronaphthalene, alkylated naphthalene or derivatives thereof, methanol, ethanol, propanol, butanol, chloroform, carbon tetrachloride, cyclohexanol, cyclohexanone, chlorobenzene, isophorone, strongly polar solvents, for example dimethylformamide, dimethyl sulfoxide, N-methylpyrrolidone, and water.

Powders, compositions for broadcasting and dusts can be prepared by mixing or joint grinding of the active substances with a solid carrier.

Granules, for example coated granules, impregnated granules and homogeneous granules, can be prepared by binding the active compounds to solid carriers. Solid carriers are, for example, mineral earths, such as silica gel, silicas, silicates, talc, kaolin, attaclay, limestone, lime, chalk, bole, loess, clay, dolomite, diatomaceous earth, calcium sulfate, magnesium sulfate, magnesium oxide, ground synthetic materials, fertilizers, such as ammonium sulfate, ammonium phosphate, ammonium nitrate, ureas and products of vegetable origin, such as cereal meal, tree bark meal, wood meal and nutshell meal, cellulose powders and other solid carriers.

The formulations generally comprise from 0.01 to 95% by weight, preferably from 0.1 to 90% by weight, of the active compound. The active compounds are employed in a purity of from 90% to 100%, preferably from 95% to 100% (according to the NMR spectrum).

Examples of formulations are:

I. 5 parts by weight of a compound according to the invention are intimately mixed with 95 parts by weight of finely divided kaolin. This affords a dust comprising 5% by weight of the active compound.

II. 30 parts by weight of a compound according to the invention are intimately mixed with a mixture of 92 parts by weight of pulverulent silica gel and 8 parts by weight of paraffin oil which have been sprayed onto the surface of this silica gel. This affords an active compound preparation having good adhesive properties (active compound content 23% by weight).

III. 10 parts by weight of a compound according to the invention are dissolved in a mixture comprising 90 parts by weight of xylene, 6 parts by weight of the addition product of 8 to 10 mol of ethylene oxide to 1 mol of oleic acid N-monoethanolamide, 2 parts by weight of the calcium salt of dodecylbenzenesulfonic acid and 2 parts by weight of the addition product of 40 mol of ethylene oxide to 1 mol of castor oil (active compound content 9% by weight).

IV. 20 parts by weight of a compound according to the invention are dissolved in a mixture comprising 60 parts by weight of cyclohexanone, 30 parts by weight of isobutanol, 5 parts by weight of the addition product of 7 mol of ethylene oxide to 1 mol of isooctylphenol and 5 parts by weight of the addition product of 40 mol of ethylene oxide to 1 mol of castor oil (active compound content 16% by weight).

V. 80 parts by weight of a compound according to the invention are intimately mixed with 3 parts by weight of the sodium salt of diisobutylnaphthalene-alpha-sulfonic acid, 10 parts by weight of the sodium salt of a lignosulfonic acid from a sulfite waste liquor and 7 parts by weight of pulverulent silica gel, well mixed and ground in a hammer mill (active compound content 80% by weight).

VI. 90 parts by weight of a compound according to the invention are mixed with 10 parts by weight of N-methyl-α-pyrrolidone, affording a solution which is suitable for use in the form of very small drops (active compound content 90% by weight).

VII. 20 parts by weight of a compound according to the invention are dissolved in a mixture comprising 40 parts by weight of cyclohexanone, 30 parts by weight of isobutanol, 20 parts by weight of the addition product of 7 mol of ethylene oxide to 1 mol of isooctylphenol and 10 parts by weight of the addition product of 40 mol of ethylene oxide to 1 mol of castor oil. The solution is poured onto 100,000 parts by weight of water and finely dispersed therein, affording an aqueous dispersion comprising 0.02% by weight of active compound.

VIII. 20 parts by weight of a compound according to the invention are intimately mixed with 3 parts by weight of the sodium salt of diisobutylnaphthalene-α-sulfonic acid, 17 parts by weight of the sodium salt of a lignosulfonic acid from a sulfite waste liquor and 60 parts by weight of pulverulent silica gel, and ground in a hammer mill. The mixture is finely dispersed in 20,000 parts by weight of water, affording a spray liquor comprising 0.1% by weight of active compound.

IX. 10 parts by weight of the compound according to the invention are dissolved in 63 parts by weight of cyclohexanone, 27 parts by weight of dispersant (for example a mixture of 50 parts by weight of the addition product of 7 mol of ethylene oxide to 1 mol of isooctylphenol and 50 parts by weight of the addition product of 40 mol of ethylene oxide to 1 mol of castor oil). The stock solution is then diluted to the desired concentration by dispersion in water, for example to a concentration in the range from 1 to 100 ppm.

The active compounds can be applied as such, in the form of their formulations or in the application forms prepared therefrom, for example in the form of directly sprayable solutions, powders, suspensions or dispersions, emulsions, oil dispersions, pastes, dusts, compositions for broadcasting, or granules, by spraying, atomizing, dusting, broadcasting or watering. The application forms depend entirely on the intended uses; in any case, they should ensure very fine dispersion of the active compounds according to the invention.

Aqueous use forms can be prepared from emulsion concentrates, pastes or wettable powders (spray powders, oil dispersions) by addition of water. To prepare emulsions, pastes or oil dispersions, the substances can be homogenized in water as such or dissolved in an oil or solvent, by means of wetting agents, tackifiers, dispersants or emulsifiers. However, concentrates comprising active compound, wetting agent, tackifier, dispersant or emulsifier and possibly solvent or oil which are suitable for dilution with water can also be prepared.

The active compound concentrations in the ready-to-use preparations can be varied over a relatively wide range. In general, they are from 0.0001 to 10%. Frequently, even low amounts of the active compound I in the ready-to-use preparation are sufficient, for example 2 to 200 ppm. Preference is also given to ready-to-use preparations having active compound concentrations in the range from 0.01 to 1%.

It is also possible to use the active compounds with a high degree of success in the ultra-low-volume method (ULV), it being possible to apply formulations comprising more than 95% by weight of active compound or even the active compound without additives.

Oils of various types, herbicides, fungicides, other pesticides and bactericides can be added to the active compounds, if desired even immediately prior to application (tank mix). These agents can be added to the compositions according to the invention in a weight ratio of 1:10 to 10:1.

The compositions according to the invention in the use form as fungicides may also be present in combination with other active compounds, for example with herbicides, insecticides, growth regulators, fungicides or else with fertilizers. In many cases, a mixture of the compounds I, or of the compositions comprising them, in the use form as fungicides with other fungicides results in a broader fungicidal spectrum of activity.

The following list of fungicides in combination with which the compounds according to the invention can be used is intended to illustrate the possible combinations, but not to impose any limitation:

- sulfur, dithiocarbamates and their derivatives, such as iron(III) dimethyldithiocarbamate, zinc dimethyldithiocarbamate, zinc ethylenebisdithiocarbamate, manganese ethylenebisdithiocarbamate, manganese zinc ethylenediaminebisdithiocarbamate, tetramethylthiuram disulfide, ammonia complex of zinc (N,N-ethylenebisdithiocarbamate), ammonia complex of zinc (N,N'-propylenebisdithiocarbamate), zinc (N,N'-propylenebisdithiocarbamate), N,N'-polypropylenebis(thiocarbamoyl)disulfide;
- nitro derivatives, such as dinitro-(1-methylheptyl)phenyl crotonate, 2-sec-butyl-4,6-dinitrophenyl-3,3-dimethyl acrylate, 2-sec-butyl-4,6-dinitrophenylisopropyl carbonate, diisopropyl 5-nitroisophthalate;
- heterocyclic substances, such as 2-heptadecyl-2-imidazoline acetate, 2-chloro-N-(4'-chlorobiphenyl-2-yl)nicotinamide, 2,4-dichloro-6-(o-chloroanilino)-s-triazine, O,O-diethyl phthalimidophosphonothioate, 5-amino-1-[bis(dimethylamino)phosphinyl]-3-phenyl-1,2,4-triazole, 2,3-dicyano-1,4-dithioanthraquinone, 2-thio-1,3-dithiolo[4,5-b]quinoxaline, methyl 1-(butylcarbamoyl)-2-benzimidazolecarbamate, 2-methoxycarbonylaminobenzimidazole, 2-(fur-2-yl)benzimidazole, 2-(thiazol-4-yl)benzimidazole, N-(1,1,2,2-tetrachloroethylthio)tetrahydrophthalimide, N-trichloromethylthiotetrahydrophthalimide, N-trichloromethylthiophthalimide,
- N-dichlorofluoromethylthio-N',N'-dimethyl-N-phenylsulfuric diamide, 5-ethoxy-3-trichloromethyl-1,2,3-thiadiazole, 2-thiocyanatomethylthiobenzothiazole, 1,4-dichloro-2,5-dimethoxybenzene, 4-(2-chlorophenylhydrazono)-3-methyl-5-isoxazolone, pyridine 2-thio-1-oxide, 8-hydroxyquinoline or its copper salt, 2,3-dihydro-5-carboxanilido-6-methyl-1,4-oxathiine, 2,3-dihydro-5-carboxanilido-6-methyl-1,4-oxathiine 4,4-dioxide, 2-methyl-5,6-dihydro-4H-pyran-3-carboxanilide, 2-methylfuran-3-carboxanilide, 2,5-dimethylfuran-3-carboxanilide, 2,4,5-trimethylfuran-3-carboxanilide, N-cyclohexyl-2,5-dimethylfuran-3-carboxamide, N-cyclohexyl-N-methoxy-2,5-dimethylfuran-3-carboxamide, 2-methylbenzanilide, 2-iodobenzanilide, N-formyl-N-morpholine 2,2,2-trichloroethyl acetal, piperazine-1,4-diylbis-1-(2,2,2-trichloroethyl)formamide, 1-(3,4-dichloroanilino)-1-formylamino-2,2,2-trichloroethane, 2,6-dimethyl-N-tridecylmorpholine or its salts, 2,6-dimethyl-N-cyclododecylmorpholine or its salts, N-[3-(p-tert-butylphenyl)-2-methylpropyl]-cis-2,6-dimethylmorpholine, N-[3-(p-tert-butylphenyl)-2-methyl-propyl]piperidine, 1-[2-(2,4-dichlorophenyl)-4-ethyl-1,3-di-oxolan-2-ylethyl]-1H-1,2,4-triazole, 1-[2-(2,4-dichloro-phenyl)-4-n-propyl-1,3-dioxolan-2-ylethyl]-1H-1,2,4-triazole, N-(n-propyl)-N-(2,4,6-trichlorophenoxyethyl)-N'-imidazolylurea, 1-(4-chlorophenoxy)-3,3-dimethyl-1-(1H-1,2,4-triazol-1-yl)-2-butanone, 1-(4-chlorophenoxy)-3,3-dimethyl-1-(1H-1,2,4-triazol-1-yl)-2-butanol, (2RS, 3RS)-1-[3-(2-chlorophenyl)-2-(4-fluorophenyl)oxiran-2-ylmethyl]-1H-1,2,4-triazole, α-(2-chlorophenyl)-α-(4-chlorophenyl)-5-pyrimidinemethanol, 5-butyl-2-dimethylamino-4-hydroxy-6-methylpyrimidine, bis(p-chlorophenyl)-3-pyridinemethanol, 1,2-bis(3-ethoxycarbonyl-2-thioureido)benzene, 1,2-bis(3-methoxycarbonyl-2-thioureido)benzene, strobilurins, such as methyl E-methoxyimino-[α-(o-tolyloxy)-o-tolyl]acetate, methyl E-2-{2-[6-(2-cyanophenoxy)-pyridimin-4-yloxy]phenyl}-3-methoxyacrylate, methyl E-methoxyimino-[α-(2-phenoxyphenyl)]acetamide, methyl E-methoxyimino-[α-(2,5-dimethylphenoxy)-o-tolyl]acetamide, methyl E-2-{2-[(2-trifluoromethyl-pyrid-6-yl)oxymethyl]phenyl}-3-methoxyacrylate, methyl (E,E)-methoximino-{2-[1-(3-trifluoromethyl-phenyl)ethylidene-aminooxymethyl]phenyl}acetate, methyl N-(2-{[1-(4-chlorophenyl)-1H-pyrazol-3-yl]oxymethyl}phenyl)-N-methoxycarbamate,
- anilinopyrimidines, such as N-(4,6-dimethylpyrimidin-2-yl)aniline, N-[4-methyl-6-(1-propynyl)pyrimidin-2-yl]aniline, N-(4-methyl-6-cyclopropylpyrimidin-2-yl)aniline,
- phenylpyrroles, such as 4-(2,2-difluoro-1,3-benzodioxol-4-yl)pyrrole-3-carbonitrile,
- cinnamamides, such as 3-(4-chlorophenyl)-3-(3,4-dimethoxy-phenyl)acryloylmorpholide, 3-(4-fluorophenyl)-3-(3,4-dimethoxyphenyl)acryloylmorpholide,
- and a variety of fungicides, such as dodecylguanidine acetate, 1-(3-bromo-6-methoxy-2-methylphenyl)-1-(2,3,4-trimethoxy-6-methylphenyl)methanone, 3-[3-(3,5-dimethyl-2-oxycyclohexyl)-2-hydroxyethyl]glutarimide, hexachlorobenzene, methyl N-(2,6-dimethylphenyl)-N-(2-furoyl)-DL-alaninate, DL-N-(2,6-dimethylphenyl)-N-(2'-methoxyacetyl)alanine methyl ester, N-(2,6-dimethylphenyl)-N-chloroacetyl-D,L-2-aminobutyrolactone, DL-N-(2,6-dimethylphenyl)-N-(phenylacetyl)alanine methyl ester, 5-methyl-5-vinyl-3-(3,5-dichlorophenyl)-2,4-dioxo-1,3-oxazolidine, 3-(3,5-dichlorophenyl)-5-methyl-5-methoxy-methyl-1,3-oxazolidine-2,4-dione, 3-(3,5-dichlorophenyl)-1-isopropylcarbamoylhydantoin, N-(3,5-dichlorophenyl)-1,2-dimethylcyclopropane-1,2-dicarboximide, 2-cyano-[N-(ethylaminocarbonyl)-2-methoximino]acetamide, 1-[2-(2,4-dichlorophenyl)pentyl]-1H-1,2,4-triazole, 2,4-difluoro-α-(1H-1,2,4-triazolyl-1-methyl)benzohydryl alcohol, N-(3-chloro- 2,6-dinitro-4-trifluoromethylphenyl)-5-trifluoromethyl-3-chloro-2-aminopyridine, 1-((bis(4-fluorophenyl)methylsilyl)methyl)-1H-1,2,4-triazole, N,N-dimethyl-5-chloro-2-cyano-4-p-tolylimidazole-1-sulfonamide, 3,5-dichloro-N-(3-chloro-1-ethyl-1-methyl-2-oxopropyl)-4-methyl benzamide.

Synthesis of the Precursor

Preparation of (R)-3,3-dimethylbut-2-ylamine (The Synthesis was Carried out According to Scheme 1 on Page 6 of the Description)

a) Resolution of the Racemate 280 g (2.75 mol) of racemic 3,3-dimethylbut-2-ylamine were initially charged, cooled to about 15° C. and mixed with 187 g (1.42 mol) of isopropyl methoxy acetate. 3 g of Novozym® 435 (=lipase from *Candida antarctica*) were then added, and the mixture was stirred at 25–30° C. for 2 days. The optical purity of the (S)-3,3-dimethylbut-2-ylamine (S-DMBA) was then 97% ee and that of the N-(3,3-dimethylbut-2-yl)-α-methoxyacetamide (R-DMBamide) formed was 99.3% ee (conversion: 49.4%). The catalyst was filtered off with suction and washed twice with in each case 30 ml of isopropanol. The combined filtrates were separated distillatively using a thin-film evaporator. At a top pressure of 50 mbar and a mantel temperature of 140° C., a mixture of isopropanol and S-DMBA having a boiling point of 45° C. distilled off via the top. The less volatile bottom consisted of R-DMBamide and unreacted acylating agent, isopropyl methoxyacetate. This less volatile mixture was once more charged using the thin-film evaporator. This time, the mantel temperature was adjusted to 140° C. and the top pressure to 35 mbar. At 60° C., the unreacted acylating agent, isopropyl methoxy acetate, distilled off via the top. The less volatile bottom consisted of pure R-DMBamide (ee: 99.3%), yield 249 g (94%).

b) Amide Cleavage and Pure Distillation:

190 g (1.1 mol) of R-DMBamide were diluted with 100 g of triethanolamine and, with stirring, heated at 120° C. At this temperature, 150 g of 50% strength aqueous sodium hydroxide solution and then 100 g of water were introduced over a period of 2 hours. The (R)-3,3-dimethylbut-2-ylamine (R-DMBA) formed distilled off azeotropically with water (top temperature: 84–86° C.). The reflux was led through a phase separator, and the aqueous amine, which separated off as upper phase, was discharged. The lower phase (water) was recycled into the reaction flask. The mixture was boiled until the top temperature had remained above 95° C. for 6 hours. The aqueous amine that had been separated off (water content: 45%) was mixed with 100 ml of n-hexane, and the mixture was heated to reflux. At a top temperature of 61° C., a heteroazeotrope consisting of n-hexane and water distilled off. At total reflux the azeotrope was led through a phase separator and the aqueous lower phase was separated off. The upper phase was returned to the distillation flask. Once all the water had been removed azeotropically, the top temperature increased to 69° C. Using a reflux/discharge ratio of 5:1, the entrainer n-hexane was distilled off. When the temperature had reached 71° C., the reflux/discharge ratio was increased to 10:1, and an intermediate fraction was collected up to a top temperature of 103° C. The pure product distilled at 103° C. This gave 105 g (99%) of the product as a colorless liquid.

$^1$H-NMR (360 MHz, CDCl$_3$): 0.85 ppm (s, 9H), 1.00 ppm (d, J=7 Hz, 3H), 1.25 ppm (s, wide, 2H), 2.60 ppm (q, J=7 Hz, 1H).

Preparation of 5,7-dihydroxy-6-(2,4,6-trifluorophenyl)-1,2,4-triazolo[1,5-a]pyrimidine A mixture of 22 mmol of diethyl 2-(2,4,6-trifluorophenyl) malonate, 24 mmol of triethylamine and 22 mmol of 3-amino-1,2,4-triazole was heated with stirring at 180° C. for 6 hours. The reaction mixture was then cooled to 50° C., admixed with a solution of 2.2 g of sodium hydroxide in 25 ml of water and stirred for 30 minutes. The aqueous phase was washed with ether and then acidified with conc. hydrochloric acid. The precipitated colorless solid was filtered off, washed with water and diisopropyl ether and dried. The yield of the title compound was 85% (m.p.: 200–201° C.).

Preparation of 5,7-dichloro-6-(2,4,6-trifluorophenyl)-1,2,4-triazolo[1,5-a]-pyrimidine 16 mmol of 5,7-dihydroxy-6-(2,4,6-trifluorophenyl)-1,2,4-triazolo[1,5-a]-pyrimidine in 20 ml of phosphorus oxychloride were heated to the boil for 4 hours. Excess phosphorus oxychloride was distilled off. The distillation residue was cooled to room temperature and admixed with 100 ml of dichloromethane. 125 ml of water were then added at a temperature below 40° C. The organic phase was dried over sodium sulfate and the solvent was then distilled off. A colorless solid remained in the reaction vessel, with a yield of 72% (m.p.: 125–126° C.).

Synthesis of the Active Compounds

The procedures shown in the Synthesis Examples below were, with appropriate modification of the starting materials, used to obtain further compounds I. The resulting compounds are listed in the tables below, together with physical data.

EXAMPLE 1

Preparation of (R)-5-chloro-7-(3,3-dimethylbut-2-yl)amino-6-(2,4,6-trifluoro-phenyl)-1,2,4-triazolo[1,5-a]pyrimidine With stirring, a mixture of 1.4 mmol of (R)-3,3-dimethylbut-2-ylamine, 1.4 mmol of triethylamine and 10 ml of dichloromethane was introduced into a mixture of 1.4 mmol of 5,7-dichloro-6-(2,4,6-trifluorophenyl)-1,2,4-triazolo[1,5-a]-pyrimidine in 30 ml of dichloromethane. The reaction mixture was then stirred at room temperature for 16 hours and finally washed with 1 N hydrochloric acid and water. The organic phase was dried over anhydrous sodium sulfate. The solvent was distilled off under reduced pressure. The crude product was purified by silica gel column chromatography. This gave the title compound in the form of colorless crystals in a yield of 76% (m.p.: 169–171° C.).

TABLE A

IA

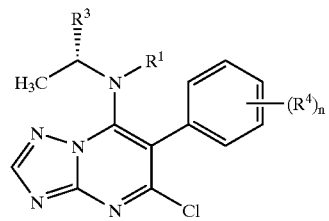

| No. | $R^1$ | $R^3$ | $(R^4)_n$ | Phys. data (m.p.[° C.]) |
|---|---|---|---|---|
| I-1 | H | $CH_2CH_3$ | 2-Cl-6-F | 147 |
| I-2 | H | $CH(CH_3)_2$ | 2-Cl-6-F | 145 |
| I-3 | H | $C(CH_3)_3$ | 2-Cl-6-F | 191 |
| I-4 | H | $CH_2CH_3$ | 2,6-$F_2$ | 176 |

TABLE A-continued

IA $$\text{structure with } R^3, R^1, H_3C, (R^4)_n, Cl, N \text{ atoms}$$

| No. | $R^1$ | $R^3$ | $(R^4)_n$ | Phys. data (m.p.[° C.]) |
|---|---|---|---|---|
| I-5 | H | $CH(CH_3)_2$ | $2,6-F_2$ | 149 |
| I-6 | H | $C(CH_3)_3$ | $2,6-F_2$ | 175 |
| I-7 | H | $CH_2CH_3$ | $2,6-Cl_2$ | 123 |
| I-8 | H | $CH(CH_3)_2$ | $2,6-Cl_2$ | 132 |
| I-9 | H | $C(CH_3)_3$ | $2,6-Cl_2$ | 216 |
| I-10 | H | $CH_2CH_3$ | $2-CH_3-6-F$ | 123 |
| I-11 | H | $CH(CH_3)_2$ | $2-CH_3-6-F$ | 116/132 |
| I-12 | H | $C(CH_3)_3$ | $2-CH_3-6-F$ | 158/203 |
| I-13 | H | $CH_2CH_3$ | $2,4,6-F_3$ | 87 |
| I-14 | H | $CH(CH_3)_2$ | $2,4,6-F_3$ | 87 |
| I-15 | H | $C(CH_3)_3$ | $2,4,6-F_3$ | 170 |
| I-16 | H | $CH_2CH_3$ | $2,6-F_2-4-OCH_3$ | 129 |
| I-17 | H | $CH(CH_3)_2$ | $2,6-F_2-4-OCH_3$ | 141 |
| I-18 | H | $C(CH_3)_3$ | $2,6-F_2-4-OCH_3$ | 186 |
| I-19 | H | $CH_2CH_3$ | $F_5$ | 99 |
| I-20 | H | $CH(CH_3)_2$ | $F_5$ | 152 |
| I-21 | H | $C(CH_3)_3$ | $F_5$ | 109 |
| I-22 | H | $CH_2CH_3$ | $2-CH_3-4-F$ | 124 |
| I-23 | H | $CH(CH_3)_2$ | $2-CH_3-4-F$ | 123 |
| I-24 | H | $C(CH_3)_3$ | $2-CH_3-4-F$ | 154 |
| I-25 | H | $CH(CH_3)_2$ | $2-CF_3$ | 154 |
| I-26 | H | $C(CH_3)_3$ | $2-CF_3$ | 142 |
| I-27 | H | $(CH_2)_3CH_3$ | $2,4,6-F_3$ | 91 |
| I-28 | H | $(CH_2)_4CH_3$ | $2,4,6-F_3$ | 189 |
| I-29 | H | $(CH_2)_5CH_3$ | $2,4,6-F_3$ | 169 |
| I-30 | H | $(CH_2)_6CH_3$ | $2,4,6-F_3$ | 175 |
| I-31 | H | cyclohexyl | $2,4,6-F_3$ | 145 |
| I-32 | H | $CH_2OCH_3$ | $2,4,6-F_3$ | 97 |
| I-33 | H | $CH_2CH_3$ | $2-CH_3-4-Cl$ | 114 |
| I-34 | H | $CH(CH_3)_2$ | $2-CH_3-4-Cl$ | 130 |
| I-35 | H | $C(CH_3)_3$ | $2-CH_3-4-Cl$ | 159 |
| I-36 | H | $CH_2CH_3$ | $2-F-4-CH_3$ | |
| I-37 | H | $CH(CH_3)_2$ | $2-F-4-CH_3$ | |
| I-38 | H | $C(CH_3)_3$ | $2-F-4-CH_3$ | |
| I-39 | H | $CH_2CH_3$ | $2-F-6-OCH_3$ | |
| I-40 | H | $CH(CH_3)_2$ | $2-F-6-OCH_3$ | |
| I-41 | H | $C(CH_3)_3$ | $2-F-6-OCH_3$ | |
| I-42 | H | $CH_2CH_3$ | $2-Cl$ | 110 |
| I-43 | H | $CH(CH_3)_2$ | $2-Cl$ | 95/112 |
| I-44 | H | $C(CH_3)_3$ | $2-Cl$ | 152/196 |

Owing to the chiral 7-amino group and the hindered rotation of the 6-phenyl group, in the case of unsymmetrical phenyl substitution, there are in each case two diastereomers which may differ in their physical properties.

USE EXAMPLES

Examples of the Activity Against Harmful Fungi

The fungicidal action of the compounds of the formula I was demonstrated by the following experiments:

The active compounds were prepared separately or jointly as a 10% strength emulsion in a mixture of 70% by weight of cyclohexanone, 20% by weight of Nekanil® LN (Lutensol® AP6, wetting agent having emulsifying and dispersing action based on ethoxylated alkylphenols) and 10% by weight of Wettol® EM (nonionic emulsifier based on ethoxylated castor oil) and diluted with water to the desired concentration.

General Remarks for Use Examples 1 to 4

In WO-A 98/46607, some of the compounds listed below are described as racemates. Furthermore, on page 7, paragraphs 1 and 2, it is emphasized that, in particular with respect to compounds having a haloalkylamine substitution in the 7-position, preference is given to the S enantiomers. The present compounds have a non-halogenated alkylamine moiety in the 7-position. Analogously, here too, an increased efficacy of the S enantiomers was to be expected. In the experiments below, the R enantiomer and the S enantiomer are in each case compared.

Use Example 1

Curative Activity Against Brown Rust of Wheat Caused by *Puccinia recondita*

Leaves of potted wheat seedlings of the cultivar "Kanzler" were dusted with spores of brown rust (*Puccinia recondita*). The pots were then placed in a chamber with high atmospheric humidity (90 to 95%) at 20–22° C. for 24 hours. During this period, the spores germinated and the germinal tubes penetrated into the leaf tissue. The following day, the infected plants were sprayed to runoff point with an aqueous preparation of active compound which had been prepared from a stock solution made of 10% of active compound, 85% of cyclohexanone and 5% of emulsifier. After the spray coating had dried on, the test plants were cultivated in a greenhouse at 20–22° C. and 65–70% relative atmospheric humidity for 7 days. The extent of the rust fungus development on the leaves was then determined.

| Active compound of Table I | % infection of the leaves after application of an aqueous preparation comprising . . . ppm of active compound | | |
|---|---|---|---|
| | 250 | 63 | 16 ppm |
| No. I.-1 (R)-amine | 0 | 3 | 5 |
| comparison (S)-amine | 15 | 20 | 60 |
| No. I.-2 (R)-amine | 5 | 5 | 15 |
| comparison (S)-amine | 100 | 100 | 100 |
| I.-3 (R)-amine | 20 | / | / |
| comparison (S)-amine | 100 | / | / |
| No. I.-4 (R)-amine | 10 | 20 | 40 |
| comparison (S)-amine | 100 | 100 | 100 |
| No. I.-5 (R)-amine | 10 | 10 | / |
| comparison (S)-amine | 100 | 100 | / |
| No. I.-7 (R)-amine | / | / | 40 |
| comparison (S)-amine | / | / | 100 |
| No. I.-10 (R)-amine | 15 | 40 | 60 |
| comparison (S)-amine | 100 | 100 | 100 |
| No. I.-11a (R)-amine | 5 | 5 | 80 |
| comparison (S)-amine | 30 | 60 | 100 |
| No. I.-11b (R)-amine | 5 | 20 | / |
| comparison (S)-amine | 100 | 100 | / |
| No. I.-13 (R)-amine | / | 0 | 3 |
| comparison (S)-amine | / | 3 | 60 |
| No. I.-14 (R)-amine | / | 0 | 0 |
| comparison (S)-amine | / | 5 | 100 |
| No. I.-15 (R)-amine | 0 | 0 | 0 |
| comparison (S)-amine | 100 | 100 | 100 |
| No. I.-16 (R)-amine | / | 0 | 7 |
| comparison (S)-amine | / | 5 | 100 |
| No. I.-22 (R)-amine | 3 | 5 | 30 |
| comparison (S)-amine | 100 | 100 | 100 |
| No. I.-23 (R)-amine | 0 | 0 | 3 |
| comparison (S)-amine | 100 | 100 | 100 |
| No. I.-27 (R)-amine | 40 | / | / |
| comparison (S)-amine | 100 | / | / |
| No. I.-32 (R)-amine | 15 | 70 | / |
| comparison (S)-amine | 80 | 100 | / |

-continued

| Active compound of Table I | % infection of the leaves after application of an aqueous preparation comprising . . . ppm of active compound | | |
|---|---|---|---|
| | 250 | 63 | 16 ppm |
| No. I.-42 (R)-amine | 5 | 20 | 30 |
| comparison (S)-amine | 15 | 60 | 100 |
| No. I.-44a (R)-amine | 60 | / | / |
| comparison (S)-amine | 100 | / | / |
| untreated | | 100 | |

Use Example 2

Activity Against Net Blotch of Barley Caused by *Pyrenophora teres*

Leaves of potted barley seedlings of the cultivar "Igri" were sprayed to runoff point with an aqueous preparation of active compound which had been prepared from a stock solution made of 10% of active compound, 85% of cyclohexanone and 5% of emulsifier and were inoculated 24 hours after the spray coating had dried on with an aqueous spore suspension of *Pyrenophora teres*, the net blotch pathogen. The test plants were then placed in a greenhouse at 20–24° C. and 95–100% relative atmospheric humidity. After 6 days, the extent of the development of the disease was determined visually in % infection of the entire leaf area.

| Active compound of Table I | % infection of the leaves after application of an aqueous preparation comprising . . . ppm of active compound | | |
|---|---|---|---|
| | 250 | 63 | 16 ppm |
| No. I.-1 (R)-amine | / | 0 | 50 |
| comparison (S)-amine | / | 20 | 100 |
| No. I.-5 (R)-amine | / | / | 20 |
| comparison (S)-amine | / | / | 80 |
| No. I.-6 (R)-amine | / | 0 | 0 |
| comparison (S)-amine | / | 5 | 60 |
| No. I.-7 (R)-amine | 15 | 30 | 80 |
| comparison (S)-amine | 100 | 100 | 100 |
| No. I.-8 (R)-amine | 15 | 15 | 40 |
| comparison (S)-amine | 100 | 100 | 100 |
| No. I.-9 (R)-amine | 0 | 0 | 0 |
| comparison (S)-amine | 100 | 100 | 100 |
| No. I.-10 (R)-amine | 3 | 3 | / |
| comparison (S)-amine | 40 | 100 | / |
| No. I.-11a (R)-amine | 0 | 0 | 5 |
| comparison (S)-amine | 100 | 100 | 100 |
| No. I.-11b (R)-amine | 0 | 15 | / |
| comparison (S)-amine | 100 | 100 | / |
| No. I.-12a (R)-amine | 0 | 0 | 0 |
| comparison (S)-amine | 100 | 100 | 100 |
| No. I.-12b (R)-amine | 0 | 7 | 7 |
| comparison (S)-amine | 100 | 100 | 100 |
| No. I.-13 (R)-amine | / | / | 20 |
| comparison (S)-amine | / | / | 60 |
| No. I.-14 (R)-amine | / | / | 3 |
| comparison (S)-amine | / | / | 40 |
| No. I.-19 (R)-amine | 30 | / | / |
| comparison (S)-amine | 80 | / | / |
| No. I.-20 (R)-amine | 0 | 10 | 30 |
| comparison (S)-amine | 7 | 40 | 100 |
| No. I.-22 (R)-amine | / | 0 | 7 |
| comparison (S)-amine | / | 7 | 80 |
| No. I.-23 (R)-amine | / | / | 0 |
| comparison (S)-amine | / | / | 60 |
| No. I.-27 (R)-amine | 0 | 0 | 3 |

-continued

| Active compound of Table I | % infection of the leaves after application of an aqueous preparation comprising . . . ppm of active compound | | |
|---|---|---|---|
| | 250 | 63 | 16 ppm |
| comparison (S)-amine | 7 | 90 | 100 |
| No. I.-28 (R)-amine | 20 | 40 | 90 |
| comparison (S)-amine | 100 | 100 | 100 |
| No. I.-31 (R)-amine | 0 | 3 | 40 |
| comparison (S)-amine | 80 | 80 | 100 |
| No. I.-32 (R)-amine | 0 | 0 | 5 |
| comparison (S)-amine | 30 | 80 | 90 |
| No. I.-44a (R)-amine | / | 7 | 60 |
| comparison (S)-amine | / | 30 | 100 |
| untreated | | 100 | |

Use Example 3

Protective Activity Against *Septoria* foliar blotch disease of wheat caused by *Septoria tritici*

Leaves of potted wheat seedlings of the cultivar "Riband" were sprayed to runoff point with an aqueous preparation of active compound which had been prepared from a stock solution made of 10% of active compound, 85% of cyclohexanone and 5% of emulsifier. 24 hours after the spray coating had dried on, they were inoculated with an aqueous spore suspension of *Septoria tritici*. The suspension contained $2.0 \times 10^6$ spores/ml. The test plants were then placed in a greenhouse at 18–22° C. and a relative atmospheric humidity of close to 100%. After 2 weeks, the extent of the development of the disease was determined visually in % infection of the entire leaf area.

| Active compound of Table I | % infection of the leaves after application of an aqueous preparation comprising . . . ppm of active compound | | |
|---|---|---|---|
| | 250 | 63 | 16 ppm |
| No. I.-2 (R)-amine | 0 | 0 | 0 |
| comparison (S)-amine | 90 | 90 | 90 |
| No. I.-4 (R)-amine | 3 | 15 | 20 |
| comparison (S)-amine | 90 | 100 | 100 |
| No. I.-5 (R)-amine | 15 | 15 | 15 |
| comparison (S)-amine | 100 | 100 | 100 |
| No. I.-7 (R)-amine | 15 | 30 | 70 |
| comparison (S)-amine | 90 | 90 | 90 |
| No. I.-8 (R)-amine | 30 | 30 | 70 |
| comparison (S)-amine | 90 | 90 | 90 |
| No. I.-14 (R)-amine | 15 | 15 | 15 |
| comparison (S)-amine | 70 | 70 | 90 |
| No. I.-16 (R)-amine | 70 | 70 | / |
| comparison (S)-amine | 90 | 90 | / |
| No. I.-17 (R)-amine | 10 | 10 | 10 |
| comparison (S)-amine | 90 | 90 | 90 |
| No. I.-18 (R)-amine | 30 | / | / |
| comparison (S)-amine | 80 | / | / |
| No. I.-19 (R)-amine | 10 | 10 | 50 |
| comparison (S)-amine | 90 | 90 | 90 |
| No. I.-20 (R)-amine | 10 | 10 | 10 |
| comparison (S)-amine | 90 | 90 | 90 |
| No. I.-25 (R)-amine | 0 | 0 | 0 |
| comparison (S)-amine | 100 | 100 | 100 |
| No. I.-26 (R)-amine | 0 | 0 | 3 |
| comparison (S)-amine | 100 | 100 | 100 |
| No. I.-44a (R)-amine | 7 | 7 | 60 |
| comparison (S)-amine | 100 | 100 | 100 |
| No. I.-44b (R)-amine | 10 | 10 | 30 |
| comparison (S)-amine | 80 | 80 | 80 |
| untreated | | 100 | |

Use Example 4

Activity Against Mildew of Wheat Caused by *Blumeria graminis* forma *specialis tritici*

Leaves of potted wheat seedlings of the cultivar "Kanzler" were sprayed to runoff point with an aqueous preparation of active compound which had been prepared from a stock solution made of 10% of active compound, 85% of cyclohexanone and 5% of emulsifier and were dusted 24 hours after the spray coating had dried on with spores of mildew of wheat (*Blumeria graminis* forma *specialis tritici*). The test plants were then placed in a greenhouse at 20–24° C. and 60–90% relative atmospheric humidity. After 7 days, the extent of the mildew development was determined visually in % infection of the entire leaf area.

| Active compound of Table I | % infection of the leaves after application of an aqueous preparation comprising . . . ppm of active compound | | |
|---|---|---|---|
| | 250 | 63 | 16 ppm |
| No. I.-2 (R)-amine | 40 | 40 | / |
| comparison (S)-amine | 100 | 100 | / |
| No. I.-4 (R)-amine | 60 | 60 | 80 |
| comparison (S)-amine | 100 | 100 | 100 |
| No. I.-5 (R)-amine | 20 | 40 | 40 |
| comparison (S)-amine | 100 | 100 | 100 |
| No. I.-6 (R)-amine | 40 | 50 | / |
| comparison (S)-amine | 90 | 90 | / |
| No. I.-7 (R)-amine | 60 | / | / |
| comparison (S)-amine | 100 | / | / |
| No. I.-10 (R)-amine | 15 | 60 | / |
| comparison (S)-amine | 100 | 100 | / |
| No. I.-11a (R)-amine | 5 | 7 | 7 |
| comparison (S)-amine | 60 | 60 | 80 |
| No. I.-11b (R)-amine | 30 | 30 | / |
| comparison (S)-amine | 60 | 60 | / |
| No. I.-12a (R)-amine | 7 | 7 | 7 |
| comparison (S)-amine | 100 | 100 | 100 |
| No. I.-12b (R)-amine | 60 | 60 | 60 |
| comparison (S)-amine | 100 | 100 | 100 |
| No. I.-13 (R)-amine | / | 40 | 60 |
| comparison (S)-amine | / | 60 | 100 |
| No. I.-14 (R)-amine | 20 | 30 | 30 |
| comparison (S)-amine | 80 | 80 | 100 |
| No. I.-15 (R)-amine | 3 | 7 | 7 |
| comparison (S)-amine | 40 | 80 | 90 |
| No. I.-16 (R)-amine | 20 | 40 | 40 |
| comparison (S)-amine | 100 | 100 | 100 |
| No. I.-17 (R)-amine | 60 | 60 | 60 |
| comparison (S)-amine | 100 | 100 | 100 |
| No. I.-19 (R)-amine | 7 | 7 | / |
| comparison (S)-amine | 30 | 30 | / |
| No. I.-20 (R)-amine | 5 | 20 | 30 |
| comparison (S)-amine | 40 | 40 | 80 |
| No. I.-22 (R)-amine | 3 | 3 | 5 |
| comparison (S)-amine | 70 | 70 | 80 |
| No. I.-23 (R)-amine | 3 | 5 | 15 |
| comparison (S)-amine | 40 | 60 | 60 |
| No. I.-24 (R)-amine | 3 | 5 | 10 |
| comparison (S)-amine | 15 | 60 | 60 |
| No. I.-31 (R)-amine | 5 | 7 | 15 |
| comparison (S)-amine | 15 | 50 | 50 |
| No. I.-44a (R)-amine | 30 | 30 | 50 |
| comparison (S)-amine | 100 | 100 | 100 |
| untreated | | 100 | |

In the above experiments, in all cases the R enantiomer shows considerably better activity than the S enantiomer.

We claim:

1. A 7-(R)-aminotriazolopyrimidine of the formula I

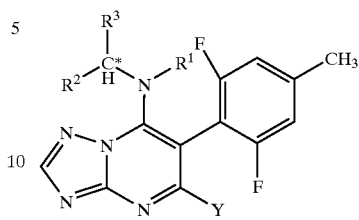

where the substituents and the index are as defined below:
$R^1$ is hydrogen or methyl;
$R^2$ is methyl;
$R^3$ is $C_2$–$C_{10}$-alkyl, $C_1$–$C_4$-alkoxymethyl, $C_3$–$C_{10}$-cycloalkyl;
Y is halogen, cyano, $C_1$–$C_4$-alkyl or $C_1$–$C_4$-alkoxy;
where * is a center of chirality in the R configuration.

2. A compound of the formula I as claimed in claim 1, where
$R^1$ is hydrogen;
$R^3$ is $C_2$–$C_{10}$-alkyl or $C_3$–$C_{10}$-cycloalkyl; and
Y is chlorine.

3. A compound of the formula I as claimed in claim 2, where
$R^3$ is tert-butyl or isopropyl.

4. A fungicidal composition, comprising solid and/or liquid carriers and a fungicidally effective amount of at least one compound of the formula I as claimed in claim 1.

5. A method for controlling phytopathogenic fungi which comprises treating the fungi or the materials, plants, seeds or the soil threatened by fungal attack with a fungicidally effective amount of at least one compound of the formula I as claimed in claim 1.

6. A process for preparing the compounds I as claimed in claim 1, which comprises
reacting a 7-halotriazolopyrimidine of the formula II,

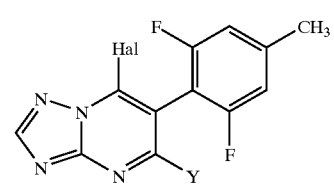

where
Hal is halogen and
Y is as defined in claim 1, with a (R)-configured amine of the formula III

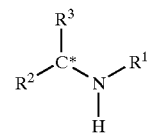

in which the substituents $R^1$, $R^2$ and $R^3$ are as defined in claim 1.

7. A process as claimed in claim 6, wherein (R)-3,3-dimethylbut-2-ylamine or (R)-3-methylbut-2-ylamine is used.

8. A process as claimed in claim 6, wherein a (R)-configured amine of the formula III is prepared by
   i) enantioselectively acylating, in the presence of a hydrolase, a racemic amine III with an ester whose acid component carries a fluorine, nitrogen, oxygen or sulfur atom in the vicinity of the carbonyl carbon,
   ii) separating the mixture of (S)-amine III and acylated (R)-amine III and
   iii) subjecting the acylated (R)-amine III to an amide cleavage.

* * * * *